United States Patent
Lalleman et al.

(10) Patent No.: US 9,993,412 B2
(45) Date of Patent: Jun. 12, 2018

(54) HAIR COLOURING METHOD EMPLOYING A CHROMENE OR CHROMAN DYE, A PARTICULAR ORGANIC COMPOUND, AN OXIDIZING AGENT, AN ALKALINE AGENT AND A METAL SALT

(71) Applicant: L'OREAL, Paris (FR)

(72) Inventors: Boris Lalleman, Paris (FR); Alain Lagrange, Coupvray (FR); Françoise Albouy, Rueil Malmaison (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 14/655,777

(22) PCT Filed: Dec. 27, 2013

(86) PCT No.: PCT/EP2013/078067
§ 371 (c)(1),
(2) Date: Jun. 26, 2015

(87) PCT Pub. No.: WO2014/102338
PCT Pub. Date: Jul. 3, 2014

(65) Prior Publication Data
US 2015/0328114 A1      Nov. 19, 2015

Related U.S. Application Data

(60) Provisional application No. 61/768,586, filed on Feb. 25, 2013.

(30) Foreign Application Priority Data

Dec. 27, 2012  (FR) ..................... 12 62866

(51) Int. Cl.
| | | |
|---|---|---|
| *A61Q 5/10* | (2006.01) | |
| *A61K 8/49* | (2006.01) | |
| *A61K 8/58* | (2006.01) | |
| *A61K 8/22* | (2006.01) | |
| *A61K 8/34* | (2006.01) | |
| *A61K 8/19* | (2006.01) | |

(52) U.S. Cl.
CPC ................ *A61K 8/498* (2013.01); *A61K 8/19* (2013.01); *A61K 8/22* (2013.01); *A61K 8/34* (2013.01); *A61K 8/58* (2013.01); *A61Q 5/10* (2013.01); *A61K 2800/884* (2013.01)

(58) Field of Classification Search
CPC . A61K 8/34; A61K 8/498; A61K 8/22; A61K 8/58; A61K 8/19; A61K 2800/884; A61Q 5/10
See application file for complete search history.

(56) References Cited

U.S. PATENT DOCUMENTS

| | | | |
|---|---|---|---|
| 4,823,985 A | 4/1989 | Grollier et al. | |
| 5,725,603 A * | 3/1998 | Audousset | ............... A61K 8/02 |
| | | | 8/405 |
| 7,833,290 B2 | 11/2010 | Guerin et al. | |
| 2010/0146718 A1* | 6/2010 | Guerin | ..................... A61K 8/19 |
| | | | 8/424 |

FOREIGN PATENT DOCUMENTS

| | | |
|---|---|---|
| EP | 2196188 A2 | 6/2010 |
| FR | 2586913 A1 | 3/1987 |
| FR | 2814943 A1 | 4/2002 |
| GB | 2190104 A | 11/1987 |
| WO | 2011/141462 A1 | 11/2011 |

OTHER PUBLICATIONS

STIC Search Report dated Apr. 14, 2016.*
International Search Report for PCT/EP2013/078067, dated Sep. 2, 2014.
English language abstract for FR 2814943 A1 (Apr. 12, 2002).

* cited by examiner

*Primary Examiner* — Eisa B Elhilo
(74) *Attorney, Agent, or Firm* — The Marbury Law Group, PLLC

(57) ABSTRACT

The present invention relates to a method for coloring keratin fibers, comprising: —a first step of applying to the fibers a dyeing composition (a) comprising one or more dyes chosen from chromene dyes and chroman dyes, and one or more liquid organic compounds having a Hansen solubility parameter δH of less than or equal to 16 Mpa$^{1/2}$, then —a second step of applying to the fibers an oxidizing composition (b) comprising one or more oxidizing agents and one or more alkaline agents, one or more metal salts and/or metal oxides being present in at least one of the compositions (a) and (b), and/or being applied during an additional step by means of a composition (c). The invention likewise relates to a kit suitable for implementing this method.

19 Claims, No Drawings

HAIR COLOURING METHOD EMPLOYING A CHROMENE OR CHROMAN DYE, A PARTICULAR ORGANIC COMPOUND, AN OXIDIZING AGENT, AN ALKALINE AGENT AND A METAL SALT

CROSS REFERENCE TO RELATED APPLICATIONS

This is a national stage application of PCT/EP2013/078067, filed internationally on Dec. 27, 2013, which claims priority to U.S. Provisional Application No. 61/768,586, filed on Feb. 25, 2013; as well as French Application 1262866, filed on Dec. 27, 2012, all of which are incorporated herein by their entireties.

The present invention relates to a method for colouring keratin fibres in two or more steps, comprising a first step of applying to said fibres a dyeing composition comprising one or more particular organic compounds and one or more dyes chosen from chromene dyes and chroman dyes, a second step of applying to the fibres an oxidizing composition comprising an oxidizing agent and an alkaline agent, and the application to the fibres of one or more metal salts and/or metal oxides either during the first or second step, or during an additional step. The invention likewise relates to a kit comprising a composition suitable for implementing such a method.

Known in the art is the dyeing of keratin fibres, and more particularly the human hair, using dyeing compositions which comprise oxidation dye precursors, referred to generally as oxidation bases, such as ortho- or para-phenylenediamines, ortho- or para-aminophenols and heterocyclic compounds. These oxidation bases are generally combined with couplers. These bases and couplers are colourless or weakly coloured compounds, which, when combined with oxidizing products, may give rise to coloured compounds by a process of oxidative condensation. This type of oxidation colouring allows permanent colourations to be obtained, but sometimes gives rise to degradation of the keratin fibres.

Also known in the art is the dyeing of keratin fibres, and more particularly the human hair, using dyeing compositions that comprise direct dyes. The conventional dyes used are, in particular, nitrobenzene, anthraquinone, nitropyridine, azo, xanthene, acridine, azine or triarylmethane dyes, or natural dyes. These dyes are coloured or colouring molecules which have a certain affinity for keratin fibres.

The compositions comprising one or more direct dyes are applied to the keratin fibres for a time required for the desired coloration to be obtained, and then rinsed off. The resulting colorations are particularly chromatic colorations, but are temporary or semi-permanent, since the nature of the interactions which bond the direct dyes to the keratin fibre, and their desorption from the surface and/or from the core of the fibre, are responsible for their weak dyeing power and their poor resistance, for example, to washing or to perspiration.

Moreover, there is increasing demand for hair colouring methods that use natural products.

Consequently there is a genuine need for development of hair colouring methods that lead to colorations that are powerful, bright, highly universal, resistant to external agents (such as, among others, light, weather, shampoos and perspiration) and that respect the nature of the hair, on the basis of compositions containing natural dyes.

These objectives are achieved by the present invention, which provides a method for colouring keratin fibres, such as human keratin fibres, and more particularly the hair, that comprises:
  a first step of applying to the fibres a dyeing composition (a) comprising one or more dyes chosen from chromene dyes and chroman dyes, and one or more liquid organic compounds having a Hansen solubility parameter $\delta H$ of less than or equal to 16 $Mpa^{1/2}$, then
  a second step of applying to the fibres an oxidizing composition (b) comprising one or more oxidizing agents and one or more alkaline agents,
the said method further comprising the application to the fibres of one or more metal salts and/or metal oxides, present in at least one of the compositions (a) and (b), and/or applied during an additional step by means of a composition (c).

The present invention likewise provides a device comprising a plurality of compartments, or dyeing kit, which is suitable for implementing the method according to the invention.

Other features, aspects and advantages of the present invention will emerge from a reading of the detailed description that follows.

The dyes used in the method according to the invention are dyes chosen from chromene dyes and chroman dyes.

According to the invention, the terms "chromene dye" and "chroman dye" mean dyes which comprise in their structure at least one bicyclic system of formula (A) below:

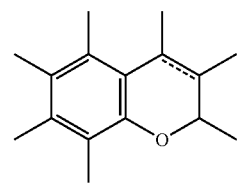

A where the endocyclic bond ---- represents a carbon-carbon single bond or else a carbon-carbon double bond, as illustrated by formula A1, denoting the class of the chromenes, and by formula A2, denoting the class of the chromans, below:

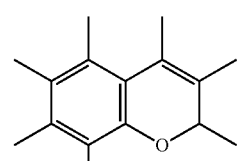

A1

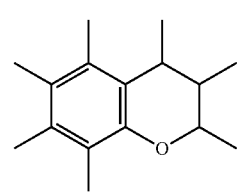

A2

More particularly the dyes of formula (A) are chosen from the compounds of formulae below:
  (i) the compounds of formula (I), comprising in their structure the bicyclic system of formula A2,

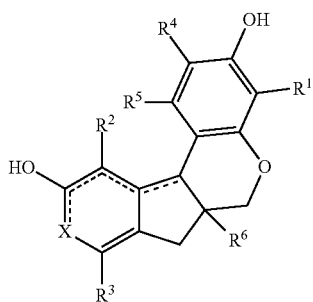

(I)

in which:

---- represents a carbon-carbon single bond or a carbon-carbon double bond, the sequence of these bonds ---- denoting two carbon-carbon single bonds and two carbon-carbon double bonds, the said bonds being conjugated, X represents a group:

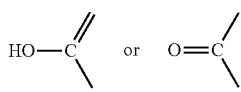

$R^1$, $R^2$, $R^3$, $R^4$, $R^5$ and $R^6$, which are identical or different, represent, independently of one another, a hydrogen atom, a hydroxyl group, an optionally substituted alkyl or optionally substituted alkoxy group, or an optionally substituted acyloxy group, and also the tautomeric and/or mesomeric forms thereof, the stereoisomers thereof, the addition salts thereof with a cosmetically acceptable acid or base, and the hydrates thereof, and (ii) the compounds of formula (II), comprising in their structure the bicyclic system of formula A1:

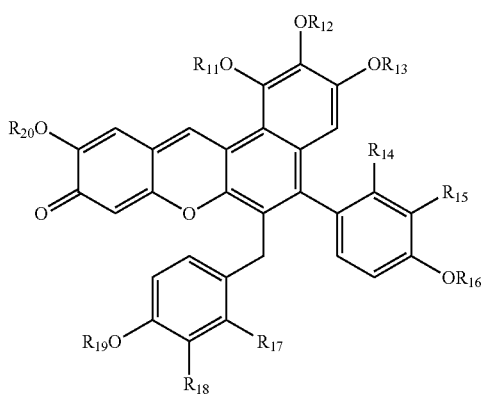

(II)

in which:

$R_{11}$, $R_{12}$, $R_{13}$, $R_{16}$, $R_{19}$ and $R_{20}$, which are identical or different, represent, independently of one another, a hydrogen atom or a $C_1$-$C_4$ alkyl radical, $R_{14}$, $R_{15}$, $R_{17}$ and $R_{18}$, which are identical or different, represent, independently of one another, a hydrogen atom, a hydroxyl radical or a $C_1$-$C_4$ alkoxy radical, and also the tautomeric and/or mesomeric forms thereof, the stereoisomers thereof, the addition salts thereof with a cosmetically acceptable acid or base, and the hydrates thereof.

With regard to the compounds of formula (I) as defined above, they may be in two tautomeric forms, identified as (Ia) and (Ib):

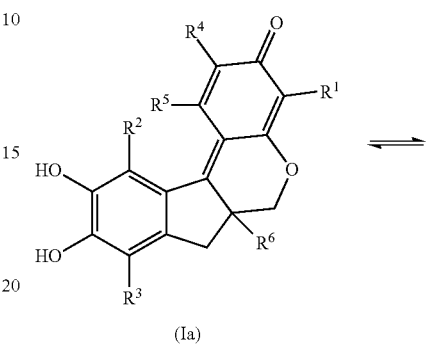

(Ia)

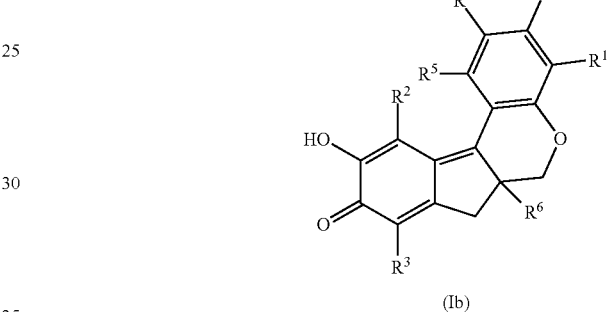

(Ib)

The alkyl radicals cited in the substituent definitions above are generally $C_1$-$C_{20}$, particularly $C_1$-$C_{10}$, preferably $C_1$-$C_6$, saturated, linear or branched, hydrocarbon radicals, such as methyl, ethyl, propyl, butyl, pentyl and hexyl.

The alkoxy radicals are alkyl-oxy radicals with the alkyl radicals as defined above, and preferably the alkoxy radicals are $C_1$-$C_{10}$ radicals, such as methoxy, ethoxy, propoxy and butoxy.

The alkyl or alkoxy radicals, when they are optionally substituted, may be substituted with at least one substituent borne by at least one carbon atom, chosen from:
  a halogen atom;
  a hydroxyl group;
  a $C_1$-$C_2$ alkoxy radical;
  a $C_1$-$C_{10}$ alkoxycarbonyl radical;
  a (poly)-$C_2$-$C_4$-hydroxyalkoxy radical;
  an amino radical;
  a 5- or 6-membered heterocycloalkyl radical;
  an optionally cationic 5- or 6-membered heteroaryl radical, preferably imidazolium, which is optionally substituted by a ($C_1$-$C_4$) alkyl radical, preferably methyl;
  an amino radical substituted by one or two, identical or different $C_1$-$C_6$ alkyl radicals which optionally carry at least:
    one hydroxyl group,
    an amino group which is optionally substituted by one or two optionally substituted $C_1$-$C_3$ alkyl radicals, it being possible for the said alkyl radicals, with the nitrogen atom to which they are attached, to form an optionally substituted, saturated or unsaturated, 5- to 7-membered heterocycle which optionally comprises at least one other nitrogen or non-nitrogen heteroatom,
a quaternary ammonium group —N⁺R'R"R"', M⁻, for which R', R", R"', which are identical or different, represent a hydrogen atom, or a $C_1$-$C_4$ alkyl group; and M⁻ represents the counter-ion of the corresponding organic or inorganic acid or halide,
or an optionally cationic 5- or 6-membered heteroaryl radical, preferably imidazolium, which is optionally substituted by a ($C_1$-$C_4$) alkyl radical, preferably methyl;
an acylamino radical (—NR—COR') in which the radical R is a hydrogen atom or a $C_1$-$C_4$ alkyl radical which optionally carries at least one hydroxyl group, and the radical R' is a $C_1$-$C_2$ alkyl radical;
a carbamoyl radical ((R)$_2$N—CO—) in which the radicals R, which are identical or not, represent a hydrogen atom or a $C_1$-$C_4$ alkyl radical which optionally carries at least one hydroxyl group;
an alkylsulfonylamino radical (R'SO$_2$—NR—) in which the radical R represents a hydrogen atom or a $C_1$-$C_4$ alkyl radical which optionally carries at least one hydroxyl group, and the radical R' represents a $C_1$-$C_4$ alkyl radical or a phenyl radical;
an aminosulfonyl radical ((R)$_2$N—SO$_2$—) in which the radicals R, which are identical or not, represent a hydrogen atom or a $C_1$-$C_4$ alkyl radical which optionally carries at least one hydroxyl group,
a carboxyl radical in acid form or salified form (preferably with an alkali metal or an ammonium which is substituted or unsubstituted);
a cyano group;
a nitro group;
a carboxyl or glycosylcarbonyl group;
a phenylcarbonyloxy group which is optionally substituted by one or more hydroxyl groups;
a glycosyloxy group; and
a phenyl group which is optionally substituted by one or more hydroxyl groups.

The term "glycosyl radical" means a radical derived from a monosaccharide or polysaccharide.

Preferably, the alkyl or alkoxy radicals of formula (I) are unsubstituted.

According to one particular embodiment of the invention, the compounds of formula (I) comprise a radical $R^6$ which represents a hydroxyl group.

Another particular embodiment of the invention relates to the compounds of formula (I), for which the radical $R^1$ represents a hydrogen atom or a hydroxyl group.

More particularly, the method for colouring keratin fibres employs, in the composition (a), one or more dyes of formula (I) chosen from haematoxylin, haematein, brazilin and brazileine.

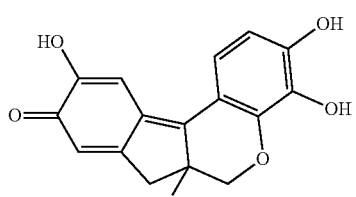

Haematein (oxidized form)

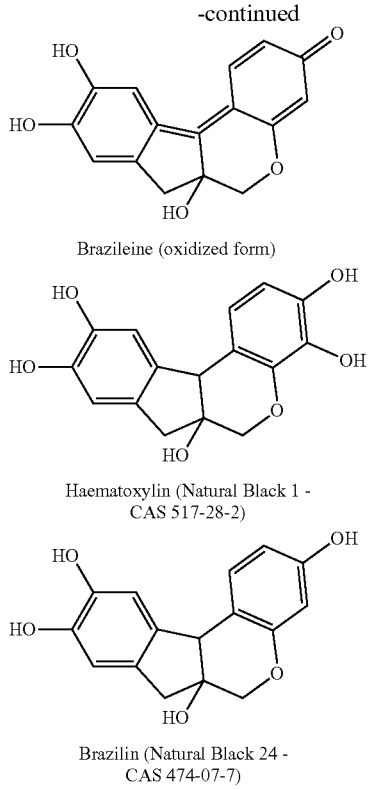

Brazileine (oxidized form)

Haematoxylin (Natural Black 1 - CAS 517-28-2)

Brazilin (Natural Black 24 - CAS 474-07-7)

Brazileine is a conjugated form of a chroman compound of formula A2. The tautomeric structures (Ia) and (Ib) illustrated above are found in the scheme below.

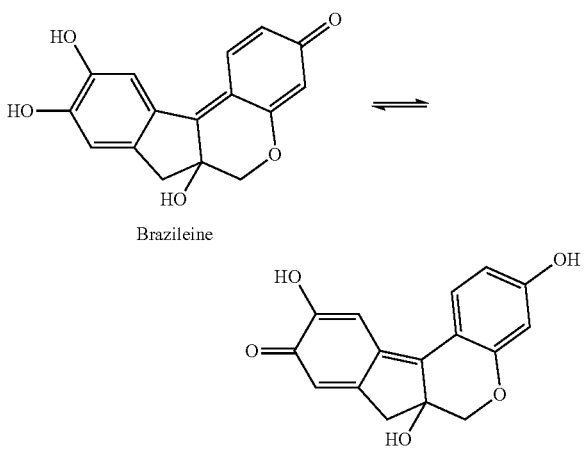

Brazileine

The haematoxylin/haematein and brazilin/brazileine compounds include, for example, haematoxylin (Natural Black 1 according to the INCI nomenclature) and brazilin (Natural Red 24 according to the INCI nomenclature), which are commercially available compounds of the indochroman class. These compounds may exist in an oxidized form and may be obtained synthetically or by extraction from plants or vegetables known to be rich in these compounds.

The compounds of formula (I) may more particularly be used in the form of extracts. Use may be made of the following plant extracts (genus and species): *Haematoxylon*

*campechianum, Haematoxylon brasiletto, Caesalpinia echinata, Caesalpinia sappan, Caesalpinia spinosa,* and *Caesalpinia brasiliensis.*

The extracts are obtained by extracting the various plant parts, for instance the root, the wood, the bark or the leaves.

According to one particular embodiment of the invention, the natural compounds of formula (I) are derived from logwood, pernambuco wood, *sappan* wood and Brazil wood.

With regard to the compounds of formula (II), the compounds used in the present invention are preferably those for which $R_{11}$ and $R_{13}$ represent an alkyl radical, preferably methyl.

Preferably, $R_{12}$, $R_{16}$, $R_{19}$ and $R_{20}$ denote, independently of one another, a hydrogen atom or an alkyl radical, preferably methyl.

Preferably, $R_{14}$ and $R_{17}$ denote, independently of one another, a hydrogen atom or an alkoxy radical, preferably methoxy.

Preferably, $R_{18}$ and $R_{15}$ denote, independently of one another, a hydrogen atom, a hydroxyl radical or an alkoxy radical, preferably methoxy.

A first particularly preferred class of compounds suitable for the present invention is that of the compounds conforming to the formula (II) above for which $R_{12}$, $R_{15}$, $R_{16}$, $R_{17}$, $R_{19}$ and $R_{20}$ each represent a hydrogen atom. $R_{11}$ and $R_{13}$ each represent a methyl radical and $R_{14}$ represents a methoxy radical.

The preferred compounds from this first class include those for which $R_{18}$ represents a methoxy radical (santalin B) or a hydroxyl radical (santalin A).

A second particularly preferred class of compounds suitable for the present invention is that of the compounds conforming to the formula (II) above for which:

$R_{11}$ and $R_{13}$ each represent a methyl radical, $R_{17}$ represents the methoxy radical.

A preferred compound from this second class is that for which, moreover, $R_{19}$ represents a methyl radical, $R_{20}$, $R_{12}$, $R_{14}$, $R_{18}$ and $R_{16}$ each represent a hydrogen atom, and $R_{15}$ represents the hydroxyl radical (santarubin A).

A second preferred compound from this second class is that for which $R_{18}$, $R_{20}$, $R_{12}$, $R_{14}$ and $R_{16}$ represent a hydrogen atom, $R_{15}$ represents a methoxy radical, and $R_{19}$ represents a methyl radical (santarubin B).

A third preferred compound from this second class is that for which $R_{20}$, $R_{12}$, $R_{14}$, $R_{15}$, $R_{16}$ and $R_{19}$ represent hydrogen and $R_{18}$ represents the hydroxyl radical (santarubin C).

Another preferred compound from this second class is that for which $R_{15}$ represents a methoxy radical, and $R_{18}$ and $R_{14}$ represent a hydrogen atom, and $R_{20}$, $R_{12}$, $R_{16}$ and $R_{19}$ represent a methyl radical (tetra-O-methylcantarubin).

The compounds of formula (II) may in particular be used in the form of extracts. Use may be made of red wood plant extracts, encompassing generally the Asian and West African red wood species of the genus *Pterocarpus* and of the genus *Baphia*. These woods are, for example, *Pterocarpus santalinus, Pterocarpus osun, Pterocarpus soyauxii, Pterocarpus erinaceus, Pterocarpus indicus* or else *Baphia nitida*. These woods may also be called padauk, sandalwood, narrawood, camwood or barwood.

Extracts which can be used in the present invention, containing compounds of formula (II), may therefore, for example, be obtained from red sandalwood (*Pterocarpus santalinus*), by aqueous basic extraction, such as the product sold under the trade name Santal Concentré SL 709C by the company Copiaa or else by means of a solvent extraction of Santalum powder, such as the product sold under the trade name Santal Poudre SL PP by the same company, Copiaa. Also included is the aqueous-alcoholic extract of red sandalwood in powder form from the company Alban Muller.

Extracts also suitable for the present invention may be obtained from woods such as camwood (*Baphia nitida*) or else barwood (*Pterocarpus soyauxii, Pterocarpus erinaceus*); the latter, accordingly, is fractured and then ground, and a conventional alcohol extraction or an alcohol extraction by percolation is then carried out on this ground material, to give a pulverulent extract which is particularly well suited to the implementation of the present invention.

The salts of the compounds of formula (I) and (II) of the invention may be salts of cosmetically acceptable acids or bases.

The acids may be inorganic or organic. Preferably, the acid is hydrochloric acid, which results in chlorides.

The bases can be inorganic or organic. In particular, the bases are alkali metal hydroxides such as sodium hydroxide, which leads to sodium salts.

The compound or compounds of formulae (I) and/or (II) that are employed in the method according to the invention are preferably derived from plant extracts. Use may also be made of mixtures of plant extracts.

The natural extracts according to the invention can be provided in the form of powders or liquids. The extracts of the invention are preferably in powder form.

The chromene or chroman dyes used are chosen preferably from haematein, haematoxylin, brazileine, brazilin, santalin A and mixtures thereof. More preferably still, preference is given to using the dyes of formula (I), and especially haematein, haematoxylin, brazileine, brazilin, and mixtures thereof.

In one especially preferred version, haematoxylin, brazilin or mixtures thereof is or are used.

The method according to the invention preferably employs a dyeing composition (a) containing from 0.001% to 20% by weight of dyes chosen from chromene dyes and chroman dyes, relative to the total weight of the dyeing composition (a), preferably from 0.01% to 10% by weight, more preferably still from 0.1% to 5% by weight, even more preferably from 1% to 5% by weight, and even more preferably still from 2% to 5% by weight.

According to the invention, the dyeing composition (a) likewise comprises one or more liquid organic compounds having a Hansen solubility parameter δH of less than or equal to 16 Mpa$^{1/2}$, preferably strictly less than 16 Mpa$^{1/2}$.

These compounds are liquid at a temperature of 25° C. and at atmospheric pressure (760 mmHg).

The organic compound or compounds which have a Hansen solubility parameter δH as defined above are, for example, described in the reference work "Hansen solubility parameters: A user's handbook", Charles M. Hansen, CRC Press, 2000, pages 167 to 185, or else in the Handbook of Solubility Parameters and other cohesion parameters, CRC Press, pages 95 to 121 and pages 177 to 185.

This solubility parameter δH is associated with the formation of hydrogen bonds.

More particularly, the "Handbook of Solubility Parameters and other cohesion parameters", CRC Press, pages 95 to 121 and pages 177 to 185, gives the equation δH=(Σ-$^zU_h$/V)$^{1/2}$ in which:

$^zU_h$ (in J·mol$^{-1}$) describes the contributions of the functional group considered in the solubility parameters to be associated with hydrogen bonds (values in table 14 on page 183); this parameter $^zU_h$ is also described in the work "The relation between surface tension and solubility parameter in liquids", Bagda, E., Farbe Lack, 84, 212, 1978;

and V is the volume of the molecule.

The value of the solubility parameter δH is usually given for a temperature of 25° C.

The said liquid organic compound or compounds may be chosen from alkanols, aliphatic esters, ethers, aromatic alcohols, alkylaryl alcohols, aromatic acids, aliphatic acids, alkylene carbonates such as propylene carbonate, lactones such as γ-butyrolactone, and mixtures thereof.

The said liquid organic compound or compounds are preferably chosen from benzyl alcohol, phenylpropanol, phenylethanol, phenoxyethanol, linear alcohols containing from 5 to 12 carbon atoms (and, among the latter, more preferably pentanol, octanol, decanol, and mixtures thereof), and mixtures thereof.

The said liquid organic compound or compounds may be present in proportions of preferably from 1% to 40% by weight, relative to the total weight of the dyeing composition (a), and more preferably from 2% to 20% by weight.

The method according to the invention likewise employs an oxidizing composition (b) comprising one or more oxidizing agents.

The said oxidizing agent or agents are chosen preferably from the group consisting of hydrogen peroxide, urea peroxide, alkali metal bromides or ferricyanides, peroxygenated salts such as, for example, persulfates, perborates, peracids and precursors thereof, and alkali or alkaline earth metal percarbonates.

The use of hydrogen peroxide is particularly preferred.

The oxidizing agent or agents represent from 0.01% to 20%, preferably from 0.1% to 10%, more preferably from 0.5% to 5% by weight, more preferably still from 0.5% to 1.5% by weight, relative to the total weight of the composition (b).

The composition (b) likewise comprises one or more alkaline agents, which may be any agent with the capacity to increase the pH of the composition in which it is located. The alkaline agent may be a Bronsted-Lowry base or Lewis base. It may be mineral or organic.

In particular, the alkaline agent or agents may be chosen from the following:

a) aqueous ammonia, b) alkanolamines such as mono-, di- and triethanolamines, isopropanolamine, 2-amino-2-methyl-1-propanol, and derivatives thereof, c) oxyethylenated and/or oxypropylenated ethylenediamines, d) mineral or organic hydroxides, e) alkali metal silicates such as sodium metasilicates, f) preferably basic amino acids such as arginine, lysine, ornithine, citrulline and histidine, g) carbonates and bicarbonates, particularly primary, secondary or tertiary amine, alkali or alkaline-earth metal or ammonium carbonates and bicarbonates, and h) the compounds of the formula (III) below:

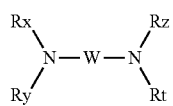

(III)

in which W is a $C_1$-$C_6$ alkylene residue which is optionally substituted by a hydroxyl group or a $C_1$-$C_6$ alkyl radical; Rx, Ry, Rz and Rt, which are identical or different, represent a hydrogen atom or a $C_1$-$C_6$ alkyl, $C_1$-$C_6$ hydroxyalkyl or $C_1$-$C_6$ aminoalkyl radical.

Examples of such compounds of formula (III) include 1,3-diaminopropane, 1,3-diamino-2-propanol, spermine and spermidine.

The mineral or organic hydroxides are preferably chosen from hydroxides of an alkali metal, hydroxides of an alkaline earth metal, such as sodium or potassium hydroxides, hydroxides of a transition metal, such as hydroxides of metals from groups III, IV, V and VI of the Periodic Table of the Elements, hydroxides of the lanthanides or the actinides, quaternary ammonium hydroxides, and guanidinium hydroxide.

The hydroxide may be formed in situ, such as, for example, guanidine hydroxide, formed by reaction of calcium hydroxide and guanidine carbonate.

The preferred alkaline agents are more particularly aqueous ammonia, sodium or ammonium carbonate, sodium or ammonium bicarbonate, arginine, monoethanolamine and 2-amino-2-methyl-1-propanol.

The alkaline agent or agents as defined above may represent, for example, from 0.1% to 20% by weight of the weight, and preferably from 1% to 15% by weight, relative to the total weight of the oxidizing composition (b).

The concentration of alkaline agent or agents is in particular adjusted depending on the desired pH for the oxidizing composition (b) when this composition is aqueous. This pH is preferably from 8 to 11, and more preferably from 8.5 to 10.

The composition (b) is preferably derived from the mixing of two compositions, one containing the oxidizing agent or agents and the other containing the alkaline agent or agents.

According to the invention, one or more metal salts and/or metal oxides are likewise applied to the fibres.

According to a first embodiment, this or these salt or salts and/or oxide or oxides are present in the dyeing composition (a) and/or in the oxidizing composition (b).

According to a second embodiment, this or these salt or salts and/or oxide or oxides are applied during an additional step, by means of a composition (c) comprising the said salt or salts and/or oxide or oxides.

In this second embodiment, the said additional step may be carried out before the first step of applying the dyeing composition (a), after the second step of applying the oxidizing composition (b), or between these two steps. It is preferably carried out after the second step of applying the oxidizing composition (b).

It is also possible to combine the two above embodiments, in other words to employ one or more metal salts and/or metal oxides in one and/or the other of the compositions (a) and (b), and to perform an additional step of applying a composition (c) containing one or more metal salts and/or metal oxides.

According to the invention, it is advantageous to employ one or more salts and/or oxides chosen from the salts and/or oxides of metals from groups 11 (IB), 12 (IIB), 2 (IIA), 13 (IIIA), 4 (IVB), 7 (VIIB), 10 (VIII) and 8 (VIIIB) of the Periodic Table of the Elements (Merck Index, 13$^{th}$ edition), and more preferably chosen from salts and/or oxides of zinc, of manganese, of iron, of copper and of aluminium.

The salts are particularly preferred. The salts include halides such as chlorides, fluorides and iodides; sulfates and phosphates; nitrates; perchlorates; and salts of carboxylic acids such as acetates, glycinates and gluconates, and polymeric salts, and also mixtures thereof.

The carboxylic salts which can be used in the invention likewise include hydroxyl-containing carboxylic salts, such as gluconate, or amine-containing carboxylic salts such as glycinate.

An example of polymeric salts includes manganese pyrrolidone carboxylate.

Non-limiting examples of manganese salts include manganese chloride, manganese fluoride, manganese acetate tetrahydrate, manganese lactate trihydrate, manganese phosphate, manganese iodide, manganese nitrate trihydrate, manganese bromide, manganese perchlorate tetrahydrate, manganese sulfate monohydrate, manganese gluconate and manganese glycinate. The manganese salts used advantageously are manganese glycinate and manganese acetate.

The salts of zinc, of iron, of copper or of aluminium include the sulfates, gluconates, chlorides, lactates, acetates, glycinates, aspartates, and citrates.

As aluminium salts it is also possible to employ one or more alums, these being one or more mixed sulfates of aluminium and a monovalent cation, chosen in particular from aluminium potassium sulfate (potassium alum), aluminium sodium sulfate (sodium alum) and aluminium and ammonium sulfate (ammonium alum).

The metal oxides and/or metal salts may be introduced in solid form into the compositions or else may originate from a natural, mineral or thermal water which is rich in these ions, or else from seawater (Dead Sea in particular). They may also originate from inorganic compounds such as earths, ochres such as clays (green clay, for example), or even from a plant extract containing them (as described, for example, in document FR 2 814 943).

The particularly preferred metal salt or salts are chosen from zinc glycinate, manganese glycinate, manganese acetate, manganese gluconate, iron gluconate, potassium, sodium or ammonium alums, and mixtures of these salts.

The metal salt or salts and/or metal oxide or oxides used represent advantageously from 0.1% to 15% by weight of the total weight of the composition or compositions containing this or these metal salts and/or metal oxides, and more preferably still from 0.5% to 12% by weight, and more preferably still from 1% to 10% by weight.

The compositions (a), (b) and (c) as defined above and employed in the method according to the invention may, independently of one another, be in various formulated forms, such as a powder, lotion, foam, cream, gel or any other form appropriate for performing the dyeing of keratin fibres. They may also be packaged in a pump dispenser without propellant, or under pressure in an aerosol canister in the presence of a propellant, and may form a foam.

These compositions advantageously comprise water, a mixture of water and one or more organic solvents, or else a mixture of organic solvents, when the composition is in liquid form.

According to one particular embodiment of the invention, at least one of the compositions (a), (b) and (c) comprises water. Preferably, the three compositions (a), (b) and (c) contain water.

Organic solvents which can be used in the compositions (a), (b) and (c), other than the particular abovementioned liquid organic compounds, include, for example, $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, and hexylene glycol.

According to another embodiment of the invention, at least one of the compositions used in the method of the invention is anhydrous and may be in a pulverulent or pasty form.

When the composition is in pulverulent form, it may comprise pulverulent ingredients.

When the composition is in the form of a paste, it may optionally comprise one or more inert organic liquids, preferably chosen from liquid petrolatum, and polydecenes and fatty esters that are liquid at ambient temperature (25° C.) and under atmospheric pressure (760 mmHg, or 1.013 bar).

The compositions employed in the colouring method in accordance with the invention may likewise include a variety of adjuvants used conventionally in compositions for the dyeing of hair, such as anionic, cationic, nonionic, amphoteric and zwitterionic surfactants or mixtures thereof, anionic, cationic, nonionic, amphoteric and zwitterionic polymers or mixtures thereof, organic or inorganic thickeners, and more particularly anionic, cationic, nonionic and amphoteric polymeric associative thickeners, antioxidants, sequestrants, fragrances, buffers, dispersants, conditioning agents such as, for example, volatile or non-volatile, modified or non-modified silicones, film formers, ceramides, preservatives and opacifiers.

The said adjuvants are chosen preferably from surfactants such as anionic or nonionic surfactants, or mixtures thereof, and from organic or inorganic thickeners.

The above adjuvants are present generally in an amount, for each of them, of between 0.01% and 40% by weight, relative to the total weight of the compositions or compositions comprising them, preferably between 0.1% and 20% by weight, relative to the total weight of the composition or compositions comprising them.

Needless to say, those skilled in the art will take care to select this or these optional additional compound(s) such that the advantageous properties intrinsically associated with the composition(s) that are of use in the dyeing process in accordance with the invention are not, or are not substantially, adversely affected by the envisaged addition(s).

The method according to the invention may employ one or more additional dyes, which may be present in the composition (a) and/or the composition (c).

These dyes may more particularly be direct dyes, which may be chosen, for example, from those conventionally used in direct colouring, and which include all of the aromatic and/or non-aromatic dyes in common use, such as neutral, acidic or cationic nitrobenzene direct dyes, neutral, acidic or cationic azo direct dyes, neutral, acidic or cationic quinone, and more particularly anthraquinone, direct dyes, azine, triarylmethane and indoamine direct dyes, methines, styryls, porphyrins, metalloporphyrins, phthalocyanines, methine cyanines, fluorescent dyes, and natural dyes other than the chromans and chromenes.

The natural direct dyes include lawsone, juglone, indigo, isatin, curcumin, spinulosin, apigenidin and orceins. Use may also be made of extracts or decoctions comprising these natural dyes and in particular henna-based poultices or extracts.

The additional dye or dyes represent preferably from 0.001% to 10% by weight, approximately, of the total weight of the composition or compositions employed.

When the chromene and/or chroman dye or dyes are in an aqueous dyeing composition (a), the pH of this composition is advantageously from 2 to 12. This pH is preferably neutral, meaning that it is from 6 to 8, and more preferably from 6.5 to 7.5.

This pH may be adjusted to the desired value by means of acidifying or alkalifying agents which are typically used in the dyeing of keratin fibres, or else by means of conventional buffer systems.

The acidifying agents include, for example, inorganic or organic acids such as hydrochloric acid, orthophosphoric acid, sulfuric acid, carboxylic acids such as acetic acid, tartaric acid, citric acid and lactic acid, and sulfonic acids.

The alkalifying agent or agents may more particularly be chosen from aqueous ammonia, alkali metal carbonates, alkanolamines such as mono-, di- and triethanolamines and also derivatives thereof, sodium hydroxide or potassium hydroxide, and the compounds of formula below:

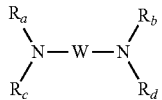

in which W is a propylene residue which is optionally substituted by a hydroxyl group or a $C_1$-$C_4$ alkyl radical; $R_a$, $R_b$, $R_c$ and $R_d$, which are identical or different, represent a hydrogen atom or a $C_1$-$C_4$ alkyl or $C_1$-$C_4$ hydroxyalkyl radical.

According to the invention, the colouring method is carried out in a plurality of steps, by sequential application to the keratin fibres of the compositions (a) and then (b) as defined above.

Accordingly, the method according to the invention comprises a first step of applying to the said fibres a dyeing composition (a) as described above, then a second step of applying to the said fibres an oxidizing composition (b) as described above.

The method may likewise include, optionally, the application of a composition (c) comprising one or more metal salts and/or metal oxides, as described above.

These steps may or may not be separated by an intermediate rinsing operation. In the absence of such intermediate rinsing, wringing may be carried out with a towel or with paper in order to remove the excess composition. An intermediate rinsing operation is preferably performed.

The leave-on time following application of the dyeing composition (a) in the said first step is generally from 3 to 120 minutes, preferably from 10 to 60 minutes, and more preferably from 15 to 45 minutes. The leave-on time after application of the oxidizing composition (b) in the said second step is generally from 3 to 120 minutes, preferably from 3 to 60 minutes, and more preferably from 5 to 30 minutes.

The temperature at which compositions (a) and (b) are applied is generally from room temperature (15 to 25° C.) to 80° C. and more particularly from 15 to 45° C. Hence it is possible, advantageously, following application of the composition according to the invention, to subject the hair to heat treatment by heating to a temperature of from 30 to 60° C. In practice, this operation may be carried out using a styling hood, a hairdryer, an infra-red ray dispenser, and other conventional heating apparatus.

It is also possible, both as a means of heating and a means of smoothing the hair, to use heating tongs at a temperature of from 60 to 220° C. and preferably from 120 to 200° C.

The invention likewise relates to the use of the method of the invention for the colouring of keratin fibres, such as human keratin fibres, and more particularly the hair.

The present invention likewise provides a multiple-compartment device or kit for the dyeing of keratin fibres, comprising at least two compartments:
  a first compartment containing a dyeing composition (a) as described above, and comprising one or more dyes chosen from chromene dyes and chroman dyes, and one or more liquid organic compounds having a Hansen solubility parameter δH of less than or equal to 16 $Mpa^{1/2}$, and
  a second compartment containing an oxidizing composition (b) as described above, and comprising one or more oxidizing agents and one or more alkaline agents,
  one or more metal salts and/or metal oxides being present in at least one of the compositions (a) and (b), and/or in an additional composition (c) contained in a third compartment.

According to one variant of the invention, the kit further comprises a compartment containing an additional composition comprising one or more treating agents. The compositions of the kit are packaged in separate compartments, which may optionally be accompanied by appropriate, identical or different, application means, such as fine brushes, coarse brushes and/or sponges.

The aforementioned kit may also be equipped with means allowing the desired mixture to be delivered to the hair, such as, for example, the device described in patent FR 2 586 913.

EXAMPLES

Example 1

The compositions (a1) and (b1) below are prepared from the ingredients set out hereinafter, the proportions of which are indicated in grams.

|  | Composition (a1) |
| --- | --- |
| Logwood extract containing 35% by weight of haematoxylin | 4 g |
| Benzyl alcohol | 4.8 g |
| Ethanol | 14.4 g |
| Bentone | 3.8 g |
| Fragrance | qs |
| Water | qs 100 g |
| pH agent | qs for pH = 6.5 |

|  | Composition (b1) |
| --- | --- |
| Sodium bicarbonate | 5 g |
| Zinc glycinate | 3.3 g |
| L-Arginine | 7 g |
| 50% Hydrogen peroxide | 2.4 g |
| Water | qs 100 g |
| pH agent | qs for pH = 9.2 |

Pairs of locks of natural Caucasian hair containing 90% white hairs are treated in succession with:

1. composition (a1), which is left on for 45 minutes at 40° C., followed by wringing, and then 2. composition (b1), which is left on for 15 minutes at 40° C.

After the application of these treatments, the locks are rinsed, shampooed, wrung and dried.

Locks are obtained which have an intense dark purple coloration and are very shiny.

The hair then underwent a test of colour retention after six shampooings.

It was observed visually that the hair coloured using the method according to the invention exhibits a very good level of shampooing resistance.

The colour of the locks before colouring, after colouring, then after shampooing was also determined by means of a spectrocolorimeter (Minolta CM3600d, D65 illuminant, 10° angle, SCI values), by measurement each time of the colorimetric values $L^*$, $a^*$ and $b^*$. In this system, $L^*$ represents the intensity of the colour, $a^*$ represents the colour on a green/red axis, and $b^*$ represents the colour on a blue/yellow axis.

The lower the value of $L^*$, the darker or more intense the colour. The higher the value of $a^*$, the redder the shade; the higher the value of $b^*$, the yellower the shade.

The variation in colour between the locks of coloured hair and the locks of uncoloured hair (control) is defined by the parameter $\Delta E$, which is calculated in accordance with the following equation:

$$\Delta E^* = \sqrt{(L^* - L_o^*)^2 + (a^* - a_o^*)^2 + (b^* - b_o^*)^2}$$

in this equation, $L^*$, $a^*$ and $b^*$ represent the values measured after colouring of the locks of hair, and $L_o^*$, $a_o^*$ and $b_o^*$ represent the values measured on the control hair prior to colouring.

The same equation enables determination of the change in colour between the coloured locks of hair and the coloured locks of hair that have undergone shampooing, with $L^*$, $a^*$ and $b^*$ representing the values measured on the coloured locks of hair which have undergone shampooing, and $L_o^*$, $a_o^*$ and $b_o^*$ representing the values measured on the coloured locks of hair prior to shampooing.

The results obtained are as follows:

| Control hair not coloured | | | Shade after colouring | | | | Shade and loss after shampooing | | | |
| --- | --- | --- | --- | --- | --- | --- | --- | --- | --- | --- |
| | | | | | | ΔE*/hair | | | | ΔE*/hair |
| $L^*$ | $a^*$ | $b^*$ | $L^*$ | $a^*$ | $b^*$ | not coloured | $L^*$ | $a^*$ | $b^*$ | coloured |
| 64.0 | 0.8 | 14.9 | 21.2 | 3.4 | −2.1 | 46.1 | 20.0 | 2.3 | −1.0 | 2.0 |

The colorimetric values above confirm that the hair coloured according to the invention exhibits a good level of shampooing resistance.

Example 2

The compositions (a2) and (b2) below are prepared from the ingredients set out hereinafter, the proportions of which are indicated in grams.

|  | Composition (a2) |
| --- | --- |
| Haematoxylin-pure logwood extract | 4 g |
| Benzyl alcohol | 4.8 g |
| Ethanol | 14.4 g |
| Zinc glycinate | 3.3 g |
| Bentone | 3.8 g |
| Fragrance | qs |
| Water | qs 100 g |

|  | Composition (b2) |
| --- | --- |
| Sodium bicarbonate | 5 g |
| L-Arginine | 7 g |
| 50% Hydrogen peroxide | 2.4 g |
| Water | qs 100 g |

Pairs of locks of natural Caucasian hair containing 90% white hairs are treated in succession with:

1. composition (a2), which is left on for 45 minutes at 40° C., followed by rinsing, and then 2. composition (b1), which is left on for 15 minutes at 40° C.

After the application of these treatments, the locks are rinsed, shampooed, wrung and dried.

Locks are obtained which have an intense purplish black coloration and are very shiny.

The hair then undergoes:

a test of colour retention after nine shampooings (using a shampoo sold under the name Elsève multi-vitamines), and a test of resistance to light (exposure for 40 hours in a Xenotest apparatus).

The colour of the locks of hair before colouring, after colouring and after shampooing or exposure to light was evaluated.

It was observed visually that the hair coloured using the method according to the invention exhibits a very good level of resistance both to shampooing and to light.

The colour of the locks before colouring, after colouring and then after shampooing and exposure to light was also determined by means of a spectrocolorimeter in the manner described in Example 1.

The results obtained are as follows:

| Control hair, not coloured | | | Shade after colouring | | | After 9 shampooings | After exposure light |
|---|---|---|---|---|---|---|---|
| | | | | | | ΔE*/hair | ΔE*/hair | ΔE*/hair |
| L* | a* | b* | L* | a* | b* | not coloured | not coloured | not coloured |
| 62.37 | 0.25 | 12.4 | 20.04 | 1.28 | −2.0 | 44.7 | 44.5 | 43.7 |

The colorimetric values above confirm that the hair coloured according to the invention exhibits a good level of resistance to shampooing and to light.

Example 3

The compositions (a3) and (b3) below are prepared from the ingredients set out hereinafter, the proportions of which are indicated in grams.

| | Composition (a3) |
|---|---|
| Haematoxylin-pure logwood extract | 4 g |
| Benzyl alcohol | 4.8 g |
| Ethanol | 14.4 g |
| Manganese gluconate | 8 g |
| Bentone | 3.8 g |
| Fragrance | qs |
| Water | qs 100 g |

| | Composition (b3) |
|---|---|
| Sodium bicarbonate | 5 g |
| L-Arginine | 7 g |
| 50% Hydrogen peroxide | 2.4 g |
| Water | qs 100 g |

Pairs of locks of natural Caucasian hair containing 90% white hairs are treated in succession with:

1. composition (a3), which is left on for 45 minutes at 40° C., followed by rinsing, and then 2. composition (b3), which is left on for 15 minutes at 40° C.

After the application of these treatments, the locks are rinsed, shampooed, wrung and dried.

Locks are obtained which have an intense black coloration and are very shiny.

The hair then undergoes a test of resistance to light (exposure for 40 hours in a Xenotest apparatus).

The colour of the locks of hair before colouring, after colouring and then after exposure to light was evaluated.

It was observed visually that the hair coloured using the method according to the invention exhibits a very good level of light resistance.

The colour of the locks before colouring, after colouring and then after exposure to light was also determined by means of a spectrocolorimeter in the manner described in Example 1.

The results obtained are as follows:

| Control hair, not coloured | | | Shade after colouring | | | | Shade after light exposure | | | |
|---|---|---|---|---|---|---|---|---|---|---|
| | | | | | | ΔE*/hair | | | | ΔE*/hair |
| L* | a* | b* | L* | a* | b* | not coloured | L* | a* | b* | not coloured |
| 62.37 | 0.25 | 12.4 | 18.22 | 0.52 | 0.16 | 45.8 | 19.38 | 0.65 | −0.07 | 44.8 |

The colorimetric values above confirm that the hair coloured according to the invention exhibits a good level of light resistance.

Example 4

The compositions (a4) and (b4) and (c4) below are prepared from the ingredients set out hereinafter, the proportions of which are indicated in grams.

| | Composition (a4) |
|---|---|
| Logwood extract containing 35% by weight of haematoxylin | 4 g |
| Benzyl alcohol | 4.8 g |
| Ethanol | 14.4 g |
| Bentone | 3.8 g |
| Fragrance | qs |
| Water | qs 100 g |

| | Composition (b4) |
|---|---|
| Sodium bicarbonate | 5 g |
| Zinc glycinate | 3.3 g |
| L-Arginine | 7 g |
| 50% Hydrogen peroxide | 2.4 g |
| Water | qs 100 g |

| | Composition (c4) |
|---|---|
| Iron gluconate | 8 g |
| Water | qs 100 g |

Locks of natural and permed Caucasian hair and natural Chinese hair, all containing 90% white hairs, are treated in succession with:

1. the composition (a4), which is left on for 45 minutes at 40° C. and then wrung, and then
2. the composition (b4), which is left on for 15 minutes at 40° C. and then rinsed, and then
3. the composition (c4), which is left on for 15 minutes at 40° C.

After the application of these treatments, the locks are rinsed, shampooed, wrung and dried.

Locks are obtained which have an intense black coloration. The coloration is shiny and highly resistant.

The invention claimed is:

1. A method for coloring keratin fibers, the method comprising:
    applying to the fibers a dyeing composition (a) comprising:
        at least one dye chosen from chromene dyes or chroman dyes, and
        at least one liquid organic compound chosen from benzyl alcohol, phenylpropanol, phenylethanol, phenoxyethanol, pentanol, octanol, decanol, or mixtures thereof;
    subsequently applying to the fibers an oxidizing composition (b) comprising at least one oxidizing agent and at least one alkaline agent; and
    applying to the fibers at least one metal salt and/or metal oxide, wherein the at least one metal salt and/or metal oxide is present in at least one of the compositions (a) or (b), and/or is applied by means of a composition (c).

2. The method according to claim 1, wherein the at least one dye chosen from chromene dyes or chroman dyes is chosen from:
    (i) compounds of formula (I):

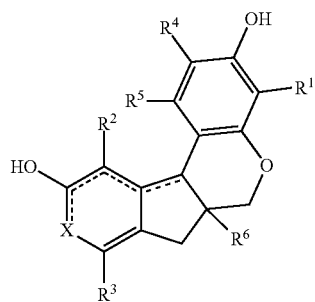

(I)

wherein:
    ═══ represents a carbon-carbon single bond or a carbon-carbon double bond, the sequence of these bonds ─── denoting two carbon-carbon single bonds and two carbon-carbon double bonds, the said bonds being conjugated,
    X represents a group:

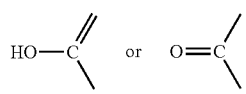

$R^1$, $R^2$, $R^3$, $R^4$, $R^5$ and $R^6$, which are identical or different, are chosen from, independently of one another, a hydrogen atom, a hydroxyl group, an optionally substituted alkyl or optionally substituted alkoxy group, or an optionally substituted acyloxy group, and also the tautomeric and/or mesomeric forms thereof, the stereoisomers thereof, the addition salts thereof with a cosmetically acceptable acid or base, or the hydrates thereof; or
    (ii) compounds of formula (II):

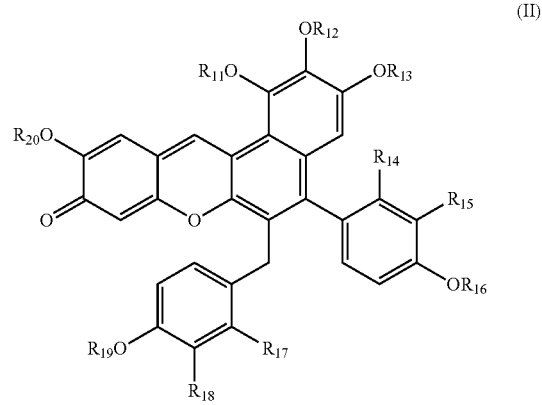

(II)

wherein:
    $R_{11}$, $R_{12}$, $R_{13}$, $R_{16}$, $R_{19}$ and $R_{20}$, which are identical or different, are chosen from, independently of one another, a hydrogen atom or a $C_1$-$C_4$ alkyl radical,
    $R_{14}$, $R_{15}$, $R_{17}$ and $R_{18}$, which are identical or different, are chosen from, independently of one another, a hydrogen atom, a hydroxyl radical, or a $C_1$-$C_4$ alkoxy radical,
    and also the tautomeric and/or mesomeric forms thereof, the stereoisomers thereof, the addition salts thereof with a cosmetically acceptable acid or base, or the hydrates thereof.

3. The method according to claim 1, wherein the at least one dye chosen from chromene dyes or chroman dyes is chosen from haematein, haematoxylin, brazileine, brazilin, santalin A, or mixtures thereof.

4. The method according to claim 1, wherein the total amount of dye chosen from chromene dyes or chroman dyes ranges from about 0.001% to about 20% by weight, relative to the total weight of the dyeing composition (a).

5. The method according to claim 1, wherein the total amount of dye chosen from chromene dyes or chroman dyes ranges from about 2% to about 5% by weight, relative to the total weight of the dyeing composition (a).

6. The method according to claim 1, wherein the total amount of liquid organic compound ranges from about 1% to about 40% by weight, relative to the total weight of the dyeing composition (a).

7. The method according to claim 1, wherein the total amount of liquid organic compound ranges from about 2% to about 20% by weight, relative to the total weight of the dyeing composition (a).

8. The method according to claim 1, wherein the at least one oxidizing agent is chosen from the group consisting of hydrogen peroxide; urea peroxide; alkali metal bromides or ferricyanides; peroxygenated salts, persulfates, perborates, peracids, and precursors thereof; or alkali or alkaline-earth metal percarbonates.

9. The method according to claim 1, wherein the total amount of oxidizing agent ranges from about 0.01% to about 20% by weight, relative to the total weight of the composition (b).

10. The method according to claim 1, wherein the total amount of oxidizing agent ranges from about 0.5% to about 1.5% by weight, relative to the total weight of the composition (b).

11. The method according to claim 1, wherein the at least one alkaline agent is chosen from:
   a) aqueous ammonia;
   b) alkanolamines, mono-, di- and triethanolamines, isopropanolamine, 2-amino-2-methyl-1-propanol, or derivatives thereof;
   c) oxyethylenated and/or oxypropylenated ethylenediamines;
   d) mineral or organic hydroxides;
   e) alkali metal silicates or sodium metasilicates;
   f) amino acids, basic amino acids, arginine, lysine, ornithine, citrulline, or histidine;
   g) carbonates or bicarbonates; or primary, secondary, or tertiary amine, alkali or alkaline-earth metal or ammonium carbonates or bicarbonates, or
   h) the compounds of the formula (III) below:

wherein:
   W is chosen from a $C_1$-$C_6$ alkylene residue which is optionally substituted by a hydroxyl group, or a $C_1$-$C_6$ alkyl radical;
   Rx, Ry, Rz and Rt, which are identical or different, are independently chosen from a hydrogen atom or a $C_1$-$C_6$ alkyl, $C_1$-$C_6$ hydroxyalkyl, or $C_1$-$C_6$ aminoalkyl radical.

12. The method according to claim 1, wherein the composition (b) has a pH ranging from about 8 to about 11.

13. The method according to claim 1, wherein the composition (b) has a pH ranging from about 8.5 to about 10.

14. The method according to claim 1, wherein the at least one metal salt and/or metal oxide is chosen from the salts and/or oxides of metals from groups 11 (IB), 12 (IIB), 2 (IIA), 13 (IIIA), 4 (IVB), 7 (VIIB), 10 (VIII), or 8 (VIIIB) of the Periodic Table of the Elements.

15. The method according claim 14, wherein the at least one metal salt is chosen from zinc glycinate, manganese glycinate, manganese acetate, manganese gluconate, iron gluconate, potassium, sodium or ammonium alums, or mixtures of these salts.

16. The method according to claim 1, wherein the total amount of metal salt and/or metal oxide ranges from about 0.1% to about 15% by weight of the total weight of the composition comprising the metal salt and/or oxides.

17. The method according to claim 1, comprising:
   applying a composition (c) comprising at least one metal salt and/or metal oxide,
   wherein applying the composition (c) is carried out before applying the dyeing composition (a), after applying the oxidizing composition (b), or between applying the dyeing composition (a) and applying the oxidizing composition (b).

18. The method according to claim 1, comprising:
   applying a composition (c) comprising at least one metal salt and/or metal oxide,
   wherein applying the composition (c) is carried out after applying the oxidizing composition (b).

19. A kit for dyeing keratin fibers, the kit comprising:
   a first compartment containing a dyeing composition (a) comprising:
      at least one dye chosen from chromene dyes or chroman dyes, and
      at least one liquid organic compound chosen from benzyl alcohol, phenylpropanol, phenylethanol, phenoxyethanol, pentanol, octanol, decanol, or mixtures thereof, and
   a second compartment containing an oxidizing composition (b) comprising:
      at least one oxidizing agent, and
      at least one alkaline agent,
   wherein at least one metal salt and/or metal oxide is present in at least one of the compositions (a) and (b), and/or in an additional composition (c) contained in a third compartment.

* * * * *